United States Patent
Bonney et al.

(10) Patent No.: US 6,651,651 B1
(45) Date of Patent: Nov. 25, 2003

(54) DISPENSER

(75) Inventors: Stanley George Bonney, Ware (GB); Anthony Patrick Jones, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/786,094

(22) PCT Filed: Aug. 26, 1999

(86) PCT No.: PCT/EP99/06249

§ 371 (c)(1),
(2), (4) Date: May 1, 2001

(87) PCT Pub. No.: WO00/12162

PCT Pub. Date: Mar. 9, 2000

(30) Foreign Application Priority Data

Aug. 28, 1998 (GB) .............................................. 9818725
Oct. 30, 1998 (GB) .............................................. 9823687

(51) Int. Cl.[7] .......................................... A61M 11/00
(52) U.S. Cl. .............................. 128/200.23; 128/203.15
(58) Field of Search .................. 128/200.14, 200.23, 128/203.12–203.15, 204.21, 204.23, 204.26, 205.23, 200.12, 200.13; 600/529, 533, 534, 535–538

(56) References Cited

U.S. PATENT DOCUMENTS

| | | | | | |
|---|---|---|---|---|---|
| 4,984,158 A | * | 1/1991 | Hillsman | ................ | 128/200.14 |
| 5,167,506 A | * | 12/1992 | Kilis et al. | ............. | 128/200.14 |
| 5,227,764 A | * | 7/1993 | Umemoto | .................... | 340/426 |
| 5,284,133 A | * | 2/1994 | Burns et al. | ........... | 128/200.14 |
| 5,333,106 A | * | 7/1994 | Lanpher et al. | ........ | 128/200.12 |
| 5,363,842 A | * | 11/1994 | Mishelevich et al. | .. | 128/200.14 |
| 5,518,002 A | * | 5/1996 | Wolf et al. | .................. | 600/538 |
| 5,544,647 A | * | 8/1996 | Jewett et al. | .......... | 128/200.23 |
| 5,622,163 A | * | 4/1997 | Jewett et al. | .......... | 128/200.19 |
| 5,735,263 A | * | 4/1998 | Rubsamen et al. | ..... | 128/200.14 |
| 5,809,997 A | * | 9/1998 | Wolf | ..................... | 128/200.23 |
| 5,899,201 A | * | 5/1999 | Schultz et al. | ......... | 128/200.23 |
| 5,956,626 A | * | 9/1999 | Kaschke et al. | ............ | 340/552 |
| 6,148,815 A | * | 11/2000 | Wolf | ..................... | 128/200.14 |
| 6,190,326 B1 | * | 2/2001 | McKinnon et al. | ......... | 600/529 |
| 6,202,642 B1 | * | 3/2001 | McKinnon et al. | .... | 128/200.23 |
| 6,358,058 B1 | * | 3/2002 | Strupat et al. | .............. | 434/262 |
| 6,481,438 B1 | * | 11/2002 | Gallem et al. | ......... | 128/205.23 |
| 6,516,799 B1 | * | 2/2003 | Greenwood et al. | ... | 128/203.12 |

FOREIGN PATENT DOCUMENTS

| | | |
|---|---|---|
| EP | 0 684 047 A | 11/1995 |
| WO | WO 93 12823 A | 7/1993 |
| WO | WO 95 07724 A | 3/1995 |
| WO | WO 96 16686 A | 6/1996 |

* cited by examiner

*Primary Examiner*—Weilun Lo
*Assistant Examiner*—Teena Mitchell
(74) *Attorney, Agent, or Firm*—James P. Riek

(57) ABSTRACT

A dispenser for dispensing medicament comprising a housing having a support; a container, locatable within said housing, having an outlet member, wherein said container is movable relative to the housing to enable dispensing therefrom and said outlet member is connectable with said support to prevent relative movement therebetween; and a detector for tracking the relative proximity of the container to the housing, said detector comprising an inductive displacement transducer including one or more inductive elements, wherein said container is comprised of, or has attached thereto a component comprised of, a material capable of disturbing the magnetic field creatable by the flow of electric current in said one or more inductive elements, and related uses and methods.

24 Claims, 7 Drawing Sheets

DISPENSER

This application is filed pursuant to 35 U.S.C. §371 as a United States National Phase Application of International Application No. PCT/EP99/06249 filed Aug. 26, 1999, which claims priority from GB9818725.5 filed Aug. 28, 1998 and GB9823687.0 filed Oct. 30, 1998.

The present invention relates to a dispenser having an actuation recorder for recording the actuation profile thereof. In particular, the invention relates to metered dose inhalers by means of which medicaments contained in an aerosol container may be administered to a patient.

It is well known to treat patients with medicaments contained in an aerosol, for example, in bronchodilator therapy. It is also known to use for such therapy, medicaments which are contained in an aerosol and are administered to a patient by means of an inhalation device comprising a tubular housing or sleeve in which the aerosol container is located and an outlet tube leading out of the tubular housing. The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the housing is then held by the patient in a more or less upright condition and the mouthpiece or nozzle of the inhalation device is placed in the mouth or nose of the patient. The aerosol container is pressed towards the support to dispense a dose of medicament from the container which is then inhaled by the patient.

It may be understood that effective delivery of medicament to the patient using an inhalation device as described above is to an extent dependent on the patient's ability to co-ordinate the actuation of the device (e.g. firing of the aerosol) with the taking of a sufficiently strong inward breath. The required coordination can present difficulties to some patients, with the risk that these patients do not receive the appropriate dose of medicament. It is thus desirable to provide a means for the patient to monitor their correct usage of the inhalation device. Such means might be designed for everyday usage, or for use in a system for training patients in the correct usage of the inhalation device.

The Applicants have now found that the actuation profile of an inhalation device may be effectively monitored by use of an inductive displacement transducer, which may simply be a coil of wire appropriately located within, or in some way associated with, the device. The coil may be connectable as the inductive element in an electronic circuit. On actuation of the device, the container is depressed and the change in inductance in the inductive element is measured. The measurements may be fed into an electronic processor, which itself may be connectable to a visual display unit which provides the advantage that the actuation profile may be visually displayed to the patient. The measurements may also be stored electronically for subsequent review and analysis.

One advantage of the use of the inductive displacement transducer to measure actuation profile is that there is no mechanical coupling of the container to the housing. Such additional mechanical coupling is inevitable in the use of switches or mechanical devices to monitor actuation.

The inductive displacement transducer may be directly attached to the housing of the dispenser. Alternatively, the inductive displacement transducer may be mounted on a carrier, which is mountable on the dispenser but separable therefrom. Where a carrier mounting is employed it would be usual to shape the carrier to be readily receivable by the housing of a standard metered dose inhaler as a removable 'add on' thereto.

The Applicants have also found that the airflow across the dispensing part of the device may be monitored by use of a pressure transducer, which measures the pressure drop across the inhaler device. In a simple embodiment, the pressure transducer is also connectable via circuitry to a visual display unit to provide a visual display of the inhalation profile, and optionally of the actuation pressure profile to the patient.

EP-A-387,222 describes an inhalation device having a detector for detecting the airflow of the inhalation and the availability of medicament at the time of inhalation. The detector can be a microphone or a pressure detector. No mention is made of the use of a displacement transducer as a detection device. Further, no mention is made of the problem of monitoring the actuation profile (versus the inhalation profile) of the device, as is addressed by the presently described invention.

U.S. Pat. No. 5,676,129 describes an inhalation device having a pressure sensor to measure pressure changes in the transfer channel of the mouthpiece of a metered dose inhaler, thereby providing a means of counting the number of doses dispensed. No mention is made of the use of a displacement transducer as a detector. No mention is made of the use of visual display of pressure profile in the training of patients in correct device usage.

It is an object to provide a dispenser having an actuation indicator which allows for patient and physician monitoring of the actuation profile and which can be employed in a system to be used in training the patient in the correct usage of the dispenser.

According to one aspect of the present invention there is provided a dispenser for dispensing medicament comprising a housing having a support; a container, locatable within said housing, having an outlet member, wherein said container is movable relative to the housing to enable dispensing therefrom and said outlet member is connectable with said support to prevent relative movement therebetween; and an inductive displacement transducer including one or more inductive elements, wherein said container is comprised of, or has attached thereto a component comprised of a material capable of disturbing the magnetic field creatable by the flow of electric current in said one or more inductive elements.

The inductive displacement transducer uses an inductive element to measure the position of the container relative to the housing. Since the inductive displacement transducer measures the relative proximity of the container to the housing it may also be thought of as an inductive proximity detector.

The container may have properties such that movement thereof relative to the one or more inductive elements is capable of causing a change in the inductance therein. The container may, for example, be comprised of a magnetic or electronically conductive material such as aluminium, or alternatively the container may have attached thereto a magnetic or electronically conductive component. The component may, for example, be a ring of material such as a ferrite ring or the component may be a coating or covering of suitable material.

Suitably, the inductive displacement transducer is engagable with the housing, such as with the exterior of the housing.

Suitably, the inductive displacement transducer is provided with mounting means for mounting of the inductive displacement transducer to the housing.

Preferably, the mounting means comprises a carrier sleeve mountable on the exterior of the housing and separable therefrom.

Suitably, the inductive displacement transducer has a plurality of inductive elements, wherein the inductive elements are magnetically or electronically couplable to each other.

Suitably, the container is an aerosol container.

Suitably, the housing is provided with an outlet, more preferably in the form of a mouthpiece. Preferably, the dispenser comprises a passage through which dispensed doses may pass from the container to the outlet.

Suitably, the container provides measured doses.

Suitably, the inductive elements comprise an electrically conductive material. In one aspect the electronically conductive material is a metal, more preferably copper or stainless steel. In another aspect the electrically conductive material is a conductive polymeric material.

The electrically conductive material is connectable as the inductive element in an electronic circuit, preferably an oscillator circuit or an AC bridge circuit. Preferably, the electronic circuit operates at a frequency of from 0.1 to 100 MHz, more-preferably 0.2 to 10 MHz.

In one aspect the electronically conductive material is a wire or tape formed into a coil. The coil may be a flat coil or may be a helical coil. Arrangements of flat or helical coils are envisaged. The turns of the coil may be electrically insulated from each other by the presence of an electrically insulating coating or by embedding in electrically insulating materials or by choice of sufficient spacing of the coils such that the air between the turns of the coil acts as an electrical insulator.

Suitably, the dispenser additionally comprises a pressure transducer.

Suitably, the dispenser is a breath operated inhaler which is actuable in response to the inward breath of a user.

According to another aspect of the present invention there is provided a system for training users in the operation of a dispenser comprising a dispenser as described above in communication with a visual unit capable of visually indicating actuation of the device by a user.

According to a further aspect of the present invention there is provided an actuation indicating device for use with a dispenser comprising a housing and a container, locatable within said housing, having an outlet member, the actuation indicating device comprising an inductive displacement transducer having mounting means to enable mounting to the housing.

In one aspect, the device records and displays the number of doses of medicament dispensed or remaining within the container following actuation thereof.

In another aspect, the device displays a symbol indicating that actuation has occurred.

In one aspect, the mounting means comprises a grip member which is engagable with the housing, preferably with the exterior of the housing.

In another aspect, the mounting means comprises a carrier sleeve mountable on the exterior of the housing and separable therefrom. A pressure transducer may also be mountable to the carrier sleeve.

The actuation indicating device and dispenser may be suppliable as a kit of parts.

According to a yet further aspect of the present invention there is provided the use of an inductive displacement transducer including one or more inductive elements to detect actuation of a dispenser for dispensing medicament, said dispenser comprising a container locatable within a housing, wherein said container is movable relative to the housing to enable dispensing therefrom, and wherein said container is comprised of, or has attached thereto a component comprised of, a material capable of disturbing the magnetic field creatable by the flow of electric current in said one or more inductive elements.

A dispenser according to the invention will now be described with reference to the accompanying drawings in which.

Figure 1:
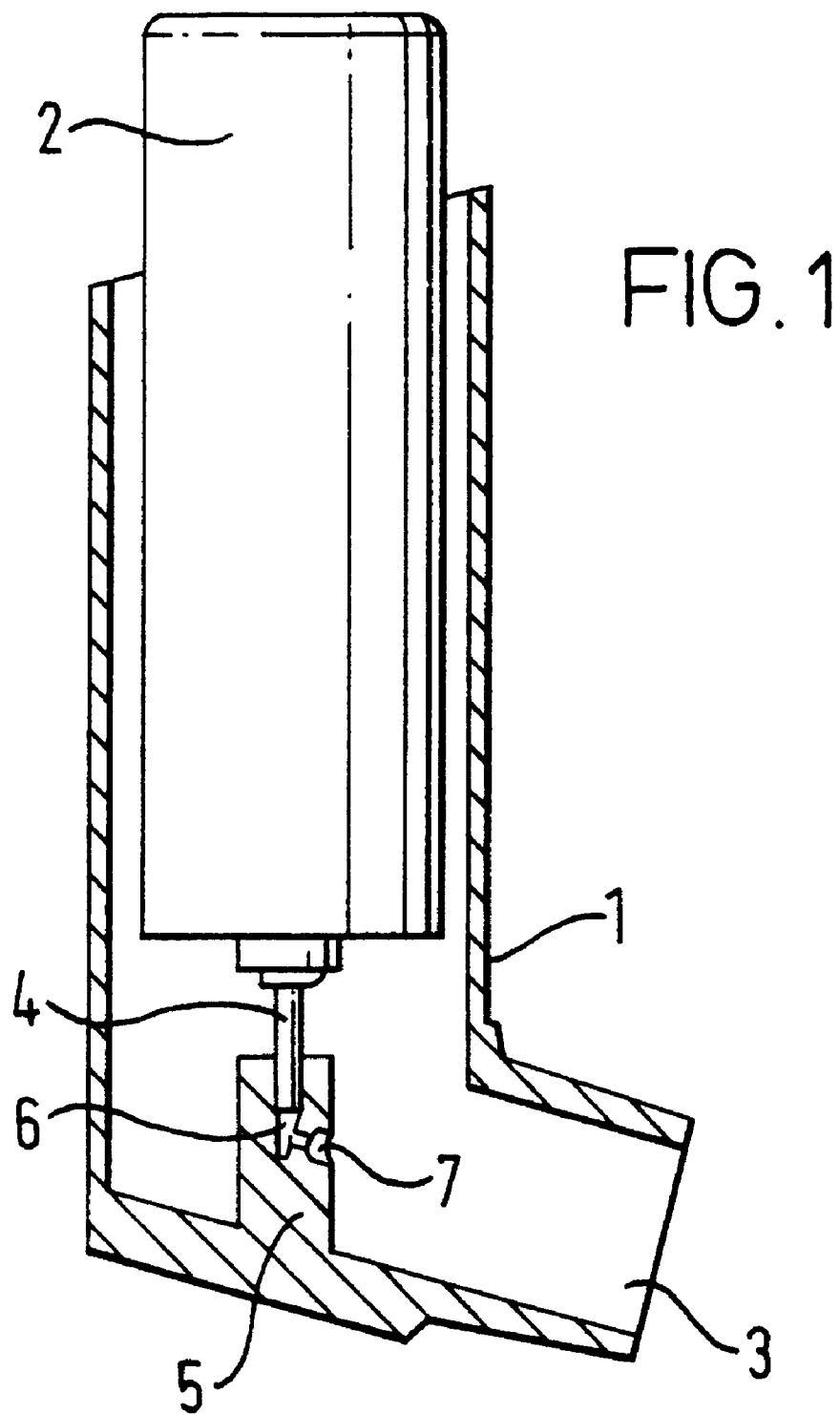
FIG. 1 is a sectional view of a known dispensing device.

The standard metered dose inhaler shown in FIG. 1 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril.

The aerosol container 2 has an outlet valve stem 4 at one end. This valve member can be depressed to release a measured dose from the aerosol container or, alternatively, the valve stem 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the container 2 spaced from the internal surface of the housing 1. A support 5 is provided at the lower end of the housing 1 and has a passage 6 in which the valve stem 4 of the aerosol container 2 can be located and supported. A second passage 7 is provided in the support 5 and is directed towards the interior of the outlet 3.

Thus, when the parts are in the positions shown in FIG. 1, the protruding portion of the aerosol container 2 can be depressed to move the container relative to the valve stem 4 to open the valve and a dose of medicament contained in the aerosol will be discharged through the passage 7 and into the outlet 3 from which it can be inhaled by a patient. One dose will be released from the aerosol container each time it is fully depressed.

Figure 2:
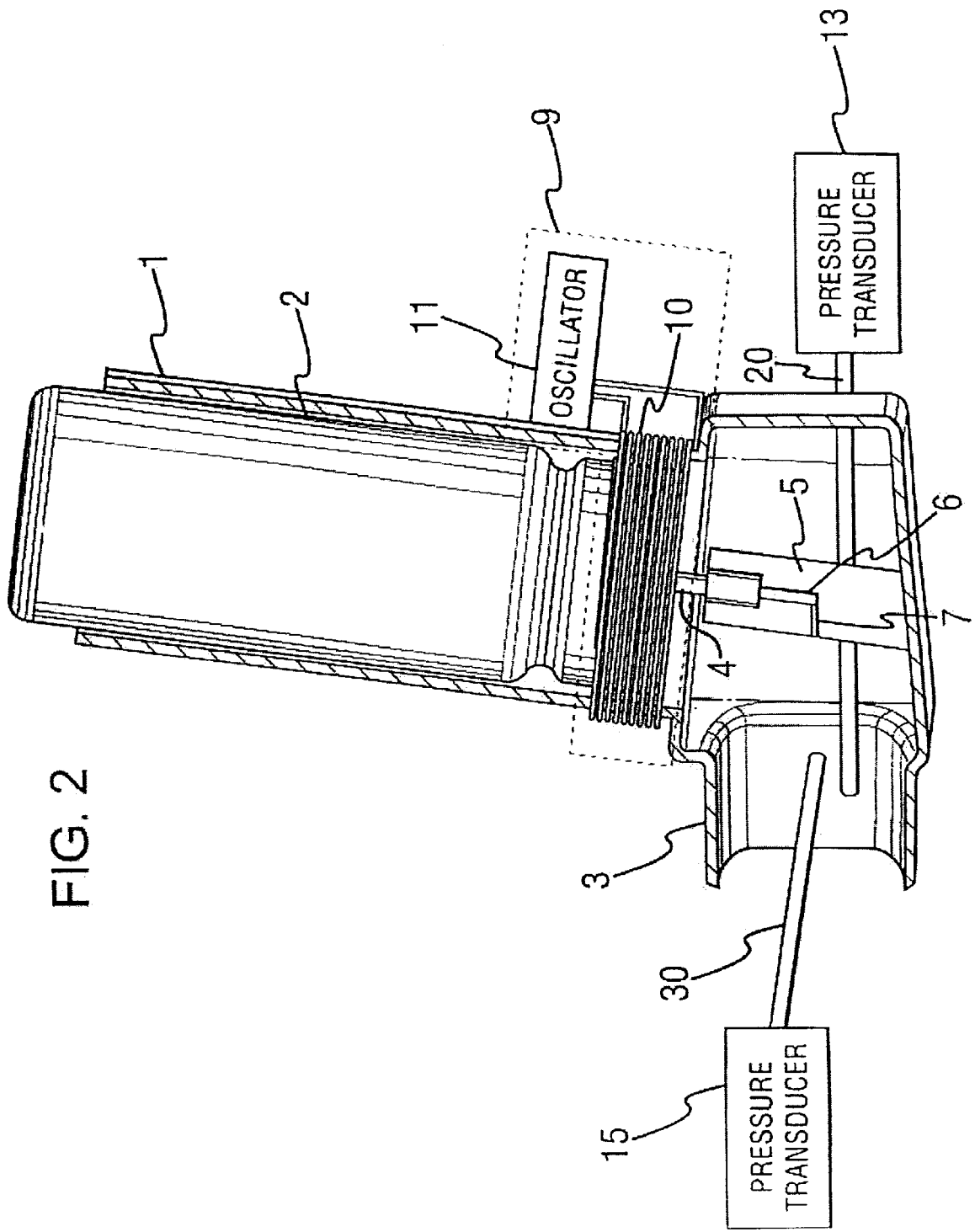
FIG. 2 is a part sectional view of a device in accord with the present invention.

FIG. 2 shows a device similar to that of FIG. 1 but incorporating an inductive displacement transducer 9 in accord with the present invention. The inductive displacement transducer 9 comprises as an inductive element a coil 10 firmly attached to the exterior of the housing 1. The inductive coil 10 is connectable as the inductive element in an electronic oscillator 11.

On actuation of the device, the protruding portion of the aerosol container 2 is moved relative to the housing 1 and inductive coil 10 attached thereto. This movement is detectable by the inductive coil since it causes a change in the inductance of the coil such that the circuit oscillates at a different frequency. The actuation can be recorded by means (not shown) of an electro-mechanical dose indicator or by an electronic device, to display the number of doses of medicament remaining or dispensed from the container 2. Alternatively the actuation may be recorded by means (not shown) of an electromechanical or an electronic indicator which displays a symbol on actuation thereby acting as a diagnostic mechanism to confirm that actuation has occurred successfully.

Figure 3:
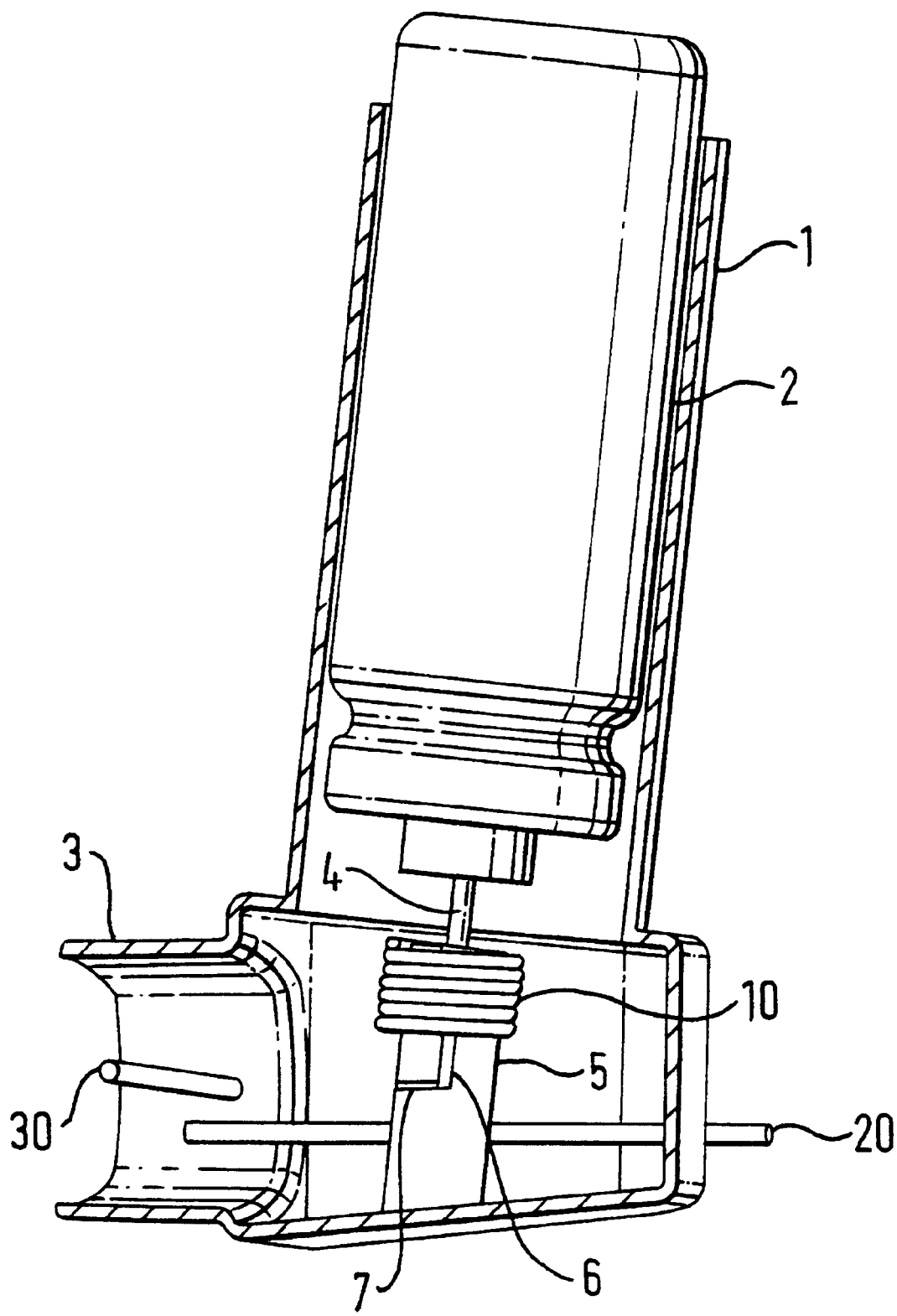
FIG. 3 is a part sectional view of a second device in accord with the present invention.

FIG. 3 shows a device, which is essentially identical to that of FIG. 2 other than that the inductive coil 10 is connected to the support 5 at the lower end of the housing 1. The positioning of the inductive coil 10 exterior to the housing 1 is advantageous since it eliminates the possibility that the presence of the coil 10 will affect the airflow profile within the device.

The devices of FIG. 2 and FIG. 3 are also provided with a first tube 20 positioned within the mouthpiece 3 wherein the first tube 20 is connectable to a first pressure transducer 13 for the measurement of pressure drop the reacross and hence enables measurement of airflow as the patient inhales.

The first pressure transducer relies for measurement on the use of the housing 1 and aerosol container 2 as a resistance element and derives the pressure across this resistance as the patient inhales.

A second tube 30 is also provided to the devices of FIG. 2 and FIG. 3 for the measurement by connection to a second pressure transducer 15 of the pressure profile on propelled release of medicament from the aerosol container 2. Subtracting therefrom the profile obtained from the first pressure transducer allows for the provision of a flat baseline for the releasprofile, even in the presence of pressure fluctuations resulting from the patient's inhalation through the mouthpiece 3. Alternatively, a differential pressure sensor could or be used to subtract one pressure measurement from the other.

Figure 4:
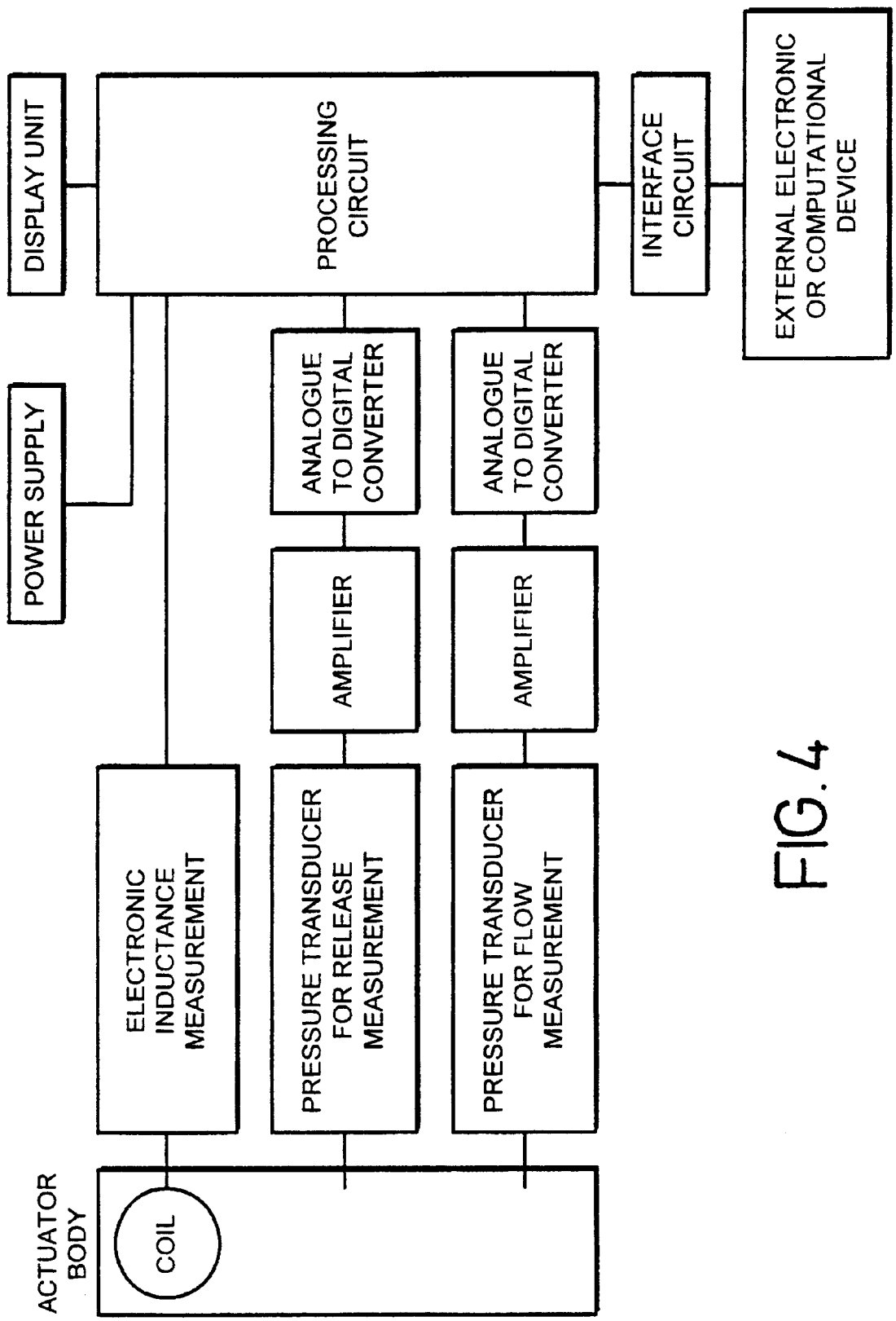
FIG. 4 is a schematic representation of a system in accord with the present invention.

The inductive coil 10 and first and second pressure transducers are each connectable to processing circuitry, which in turn may be connectable to electronic computation or information storage means. A typical system is represented schematically in FIG. 4.

Figure 5:
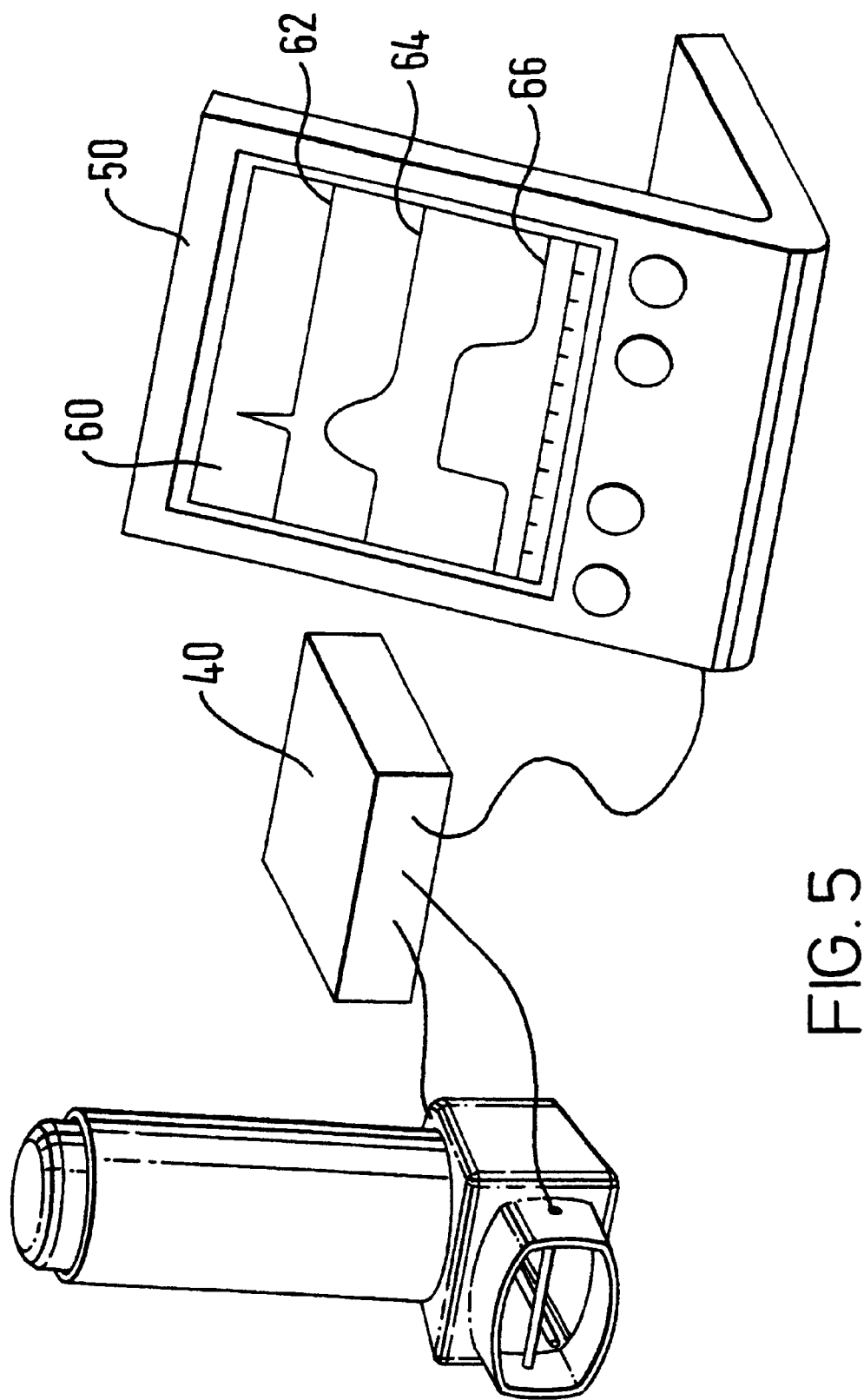
FIG. 5 is a perspective view of a training system in accord with the present invention.

The use of visual display means is of particular utility in the training of patients in the correct operation of the device, since the actuation profile, inhalation profile and release profile may be visually represented. FIG. 5 shows a suitable training system in which the device is connected to processing means 40. The processing means 40 are in turn connected to a visual display unit 50 having a display screen 60 on which are represented traces for the release 62, inhalation 64 and actuation 66 profiles.

The use of electronic computational and storage means is of particular utility in the comparison of pressure release profiles of different devices.

A variety of means of attachment of the inductive displacement transducer to the housing are envisaged including mechanical grips; adhesive attachment; use of welded shrink sleeves; heat forming; crimping; ultra-sonic welding; and by the presence of an o-ring elastomer on the housing which is fixedly piercable by barbs on the attachment member of the inductive displacement transducer. In one aspect, permanent means of attachment are preferred.

Figure 6:
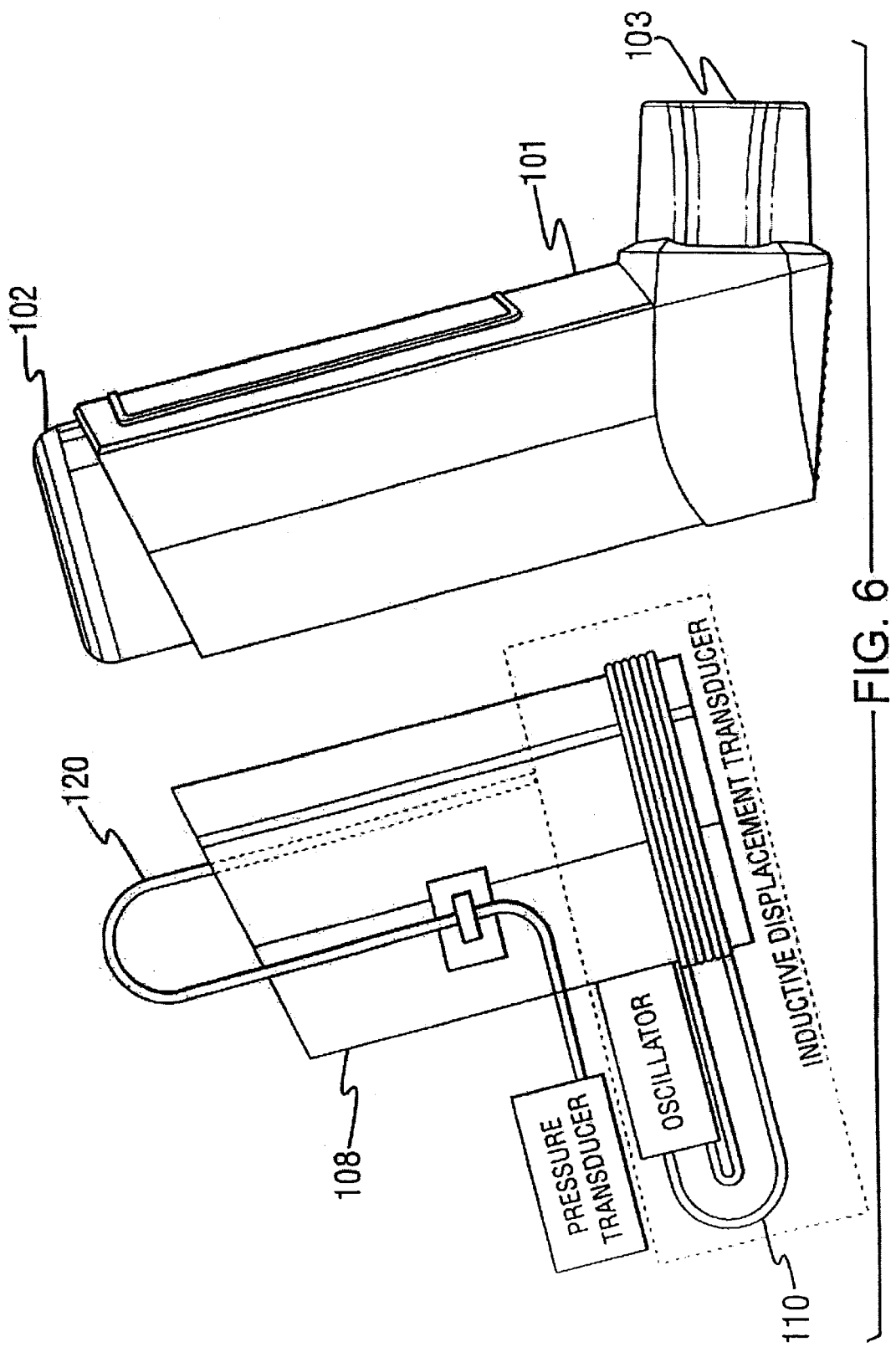
FIG. 6 is a side view of a kit of parts comprising a standard metered dose inhaler and an actuating device in accord with the present invention.

FIG. 6 shows a kit of parts comprising a standard metered dose dispenser (essentially identical to that shown in FIG. 1) and an actuation indicating device.

The metered dose inhaler comprises a tubular housing 101 containing an aerosol container 102 and having an outlet 103 in the form of a mouthpiece.

The actuator indicating device is seen to comprise a hollow tubular sleeve 108, which is sized and shaped to be receivable by the exterior of the tubular housing 101 of the dispenser. The sleeve 108 is provided with an inductive element in the form of coil 110, which is tightly wrapped therearound. The sleeve is also provided with a flexible pressure tube 120, which is connectable to means for the measurement of pressure profile.

Figure 7:
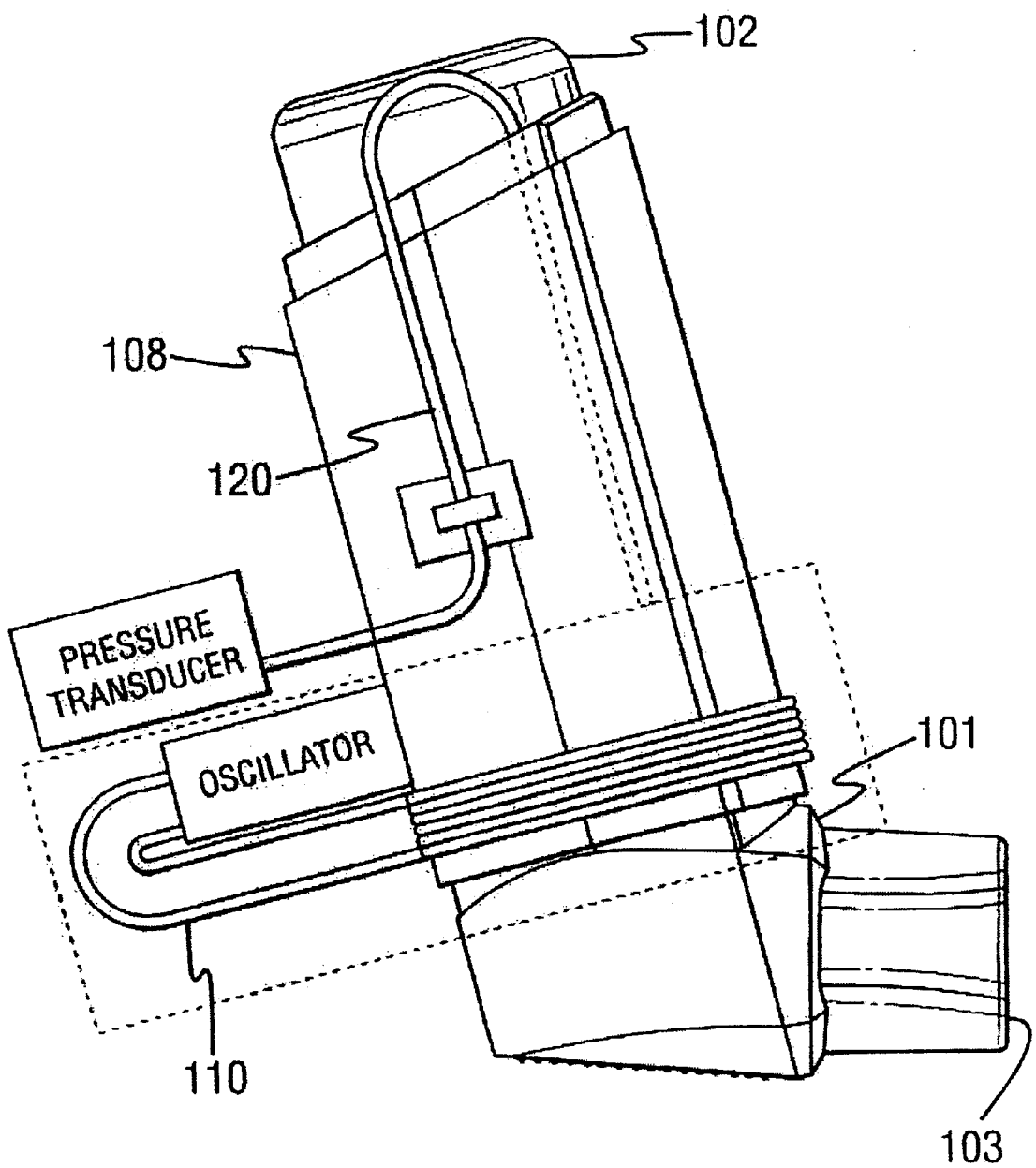
FIG. 7 is a side view of the assembled kit of parts of FIG. 6.

FIG. 7 shows the kit of parts of FIG. 6 in assembled form. It may be seen that the assembly in many ways resembles the dispenser shown at FIG. 2 other than that the coil 110 is on the sleeve 108 rather than being directly attached to the housing 101. The pressure tube 120 is also positioned slightly differently from the positioning of the first pressure tube 20 of FIG. 2. The principle of operation of the dispenser, and inductive measurement of actuation, however, corresponds to that of the dispenser of FIG. 2.

Whilst the present invention has been described in detail in respect of a metered dose inhaler actuatable manually by the patient it will be appreciated that other actuation mechanisms can be substituted. In particular, the use of a breath operated inhaler in which the actuation is assisted, and is responsive to, preferably triggered by, the inward breath of the patient, is also envisaged.

The dispenser of the invention is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, satmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. A dispenser for dispensing medicament comprising:
    a housing having a support and an exterior;
    a container, locatable within said housing, said container having an outlet member, wherein said container is movable relative to the housing to enable dispensing therefrom and said outlet member is connectable with said support to prevent relative movement therebetween; and
    a carrier sleeve mountable on and separable from the exterior of said housing, said carrier sleeve comprising a detector comprising one or more inductive displacement transducer including one or more inductive elements, said inductive displacement transducer capable of creating a magnetic field by flow of an electric current,
    wherein said container is comprised of, or has attached thereto a component comprised of, a material capable of disturbing said magnetic field, and wherein said container is movable from a first position relative to said one or more inductive element to a second position relative to said one or more inductive element and whereby said magnetic field is disturbed by movement of said container from the first to second position.

2. A dispenser according to claim 1, wherein the inductive displacement transducer includes a coil of electrically conductive material.

3. A dispenser according to claim 2, wherein the coil is helical.

4. A dispenser according to claim 1, wherein the inductive displacement transducer is engagable with the housing.

5. A dispenser according to claim 1, wherein the inductive displacement transducer has a plurality of inductive elements, which are magnetically or electrically couplable to each other.

6. A dispenser according to claim 1 wherein the container is an aerosol container.

7. A dispenser according to claim 1 wherein the housing is provided with an outlet.

8. A dispenser according to claim 7 comprising a passage through which dispensed doses may pass from the container to said outlet.

9. The dispenser according to claim 7, wherein the outlet comprises a mouthpiece.

10. A dispenser according to claim 1 wherein said container provides measured doses.

11. A dispenser according to claim 1, wherein the inductive displacement transducer is connectable as the inductive element in an electronic oscillator.

12. A dispenser according to claim 11, wherein the electronic oscillator operates at a frequency from 0.1 to 100 MHz.

13. A system of training users to operate a dispenser comprising a dispenser according to claim 1 in communication with a visual display unit capable of visually indicating actuation of the device.

14. A dispenser according to claim 1, wherein said carrier sleeve further comprises a tube and a pressure transducer connectable to said tube.

15. Use of a dispenser according to claim 1 for dispensing medicament.

16. A dispenser according to claim 1, wherein said carrier sleeve further comprises an actuation indicating device that records and displays the number of doses of medicament dispensed or remaining within the container following actuation of said dispenser.

17. A dispenser according to claim 1, wherein said carrier sleeve further comprises an actuation indicating device that displays a symbol when a dose of medicament has been dispensed on actuation of said dispenser.

18. A dispenser for dispensing medicament comprising:
    a housing having a support;
    a container, locatable within said housing, having an outlet member, wherein said container is movable relative to the housing to enable dispensing therefrom and said outlet member is connectable with said support to prevent relative movement therebetween; and
    a detector comprising one or more inductive displacement transducers including one or more inductive elements, said one or more inductive displacement transducers capable of creating a magnetic field therein by a flow of electric current,
    said container being movable from a first position relative to the one or more inductive elements to a second position relative to said one or more inductive elements thereby creating an interference in said magnetic field, and said detector able to indicate when such interference has occurred; and
    a tube connectable to a pressure transducer for measurement of pressure within the housing;
    wherein said tube comprises a first pressure tube connecting to a first pressure transducer; and said dispenser further comprises
        a second pressure tube connecting to a second pressure transducer, and
        a processing circuit in communication with said first and second pressure transducers.

19. A dispenser according to claim 18, actuable in response to an inward breath of a user.

20. The dispenser according to claim 18,
    wherein said detector detects relative movement of said dispenser and produces movement data;
    said first pressure transducer detects a first pressure profile;
    and said second pressure transducer detects a second pressure profile;
    and said movement data, said first pressure profile and said second pressure profile are communicated to said processing circuit to generate a output data in response thereto.

21. A dispenser according to claim 18, wherein said detector further comprises an actuation indicating device that records and displays the number of doses of medicament dispensed or remaining within the container following actuation of said dispenser.

22. A dispenser according to claim 18, wherein said detector further comprises an actuation indicating device that displays a symbol when a dose of medicament has been dispensed on actuation of said dispenser.

23. An inhalation device for dispensing medicament comprising a housing having a support;

a container, locatable within said housing, having an outlet member, wherein said container is movable relative to the housing to enable dispensing therefrom and said outlet member is connectable with said support to prevent relative movement therebetween;

within said housing, a first pressure tube connecting to a first pressure transducer; and a second pressure tube connecting to a second pressure transducer.

24. A method for measuring a pressure release profile on dispensing medicament to an inhaling patient from a device according to claim 23 comprising:

(a) measuring a first pressure profile as the patient inhales with said first pressure transducer;

(b) measuring a second pressure profile on dispensing of the medicament with said second pressure transducer; and (c) subtracting the first pressure profile from the second pressure profile to give a pressure release profile on dispensing of medicament.

* * * * *